US012584983B2

(12) United States Patent
Beck

(10) Patent No.: US 12,584,983 B2
(45) Date of Patent: Mar. 24, 2026

(54) METHOD FOR GENERATING A MODIFIED MAGNETIC RESONANCE SEQUENCE, MAGNETIC RESONANCE DEVICE, AND COMPUTER PROGRAM PRODUCT

(71) Applicant: Siemens Healthcare GmbH, Erlangen (DE)

(72) Inventor: Thomas Beck, Dormitz (DE)

(73) Assignee: Siemens Healthineers AG, Forchheim (DE)

( * ) Notice: Subject to any disclaimer, the term of this patent is extended or adjusted under 35 U.S.C. 154(b) by 187 days.

(21) Appl. No.: 18/523,870

(22) Filed: Nov. 29, 2023

(65) Prior Publication Data

US 2024/0183920 A1     Jun. 6, 2024

(30) Foreign Application Priority Data

Dec. 2, 2022    (DE) ..................... 10 2022 213 010.3

(51) Int. Cl.
 *G01R 33/54*       (2006.01)
 *G01R 33/36*       (2006.01)
 *G01R 33/58*       (2006.01)
 *A61B 5/055*       (2006.01)

(52) U.S. Cl.
 CPC ....... *G01R 33/543* (2013.01); *G01R 33/3607* (2013.01); *G01R 33/583* (2013.01); *A61B 5/055* (2013.01)

(58) Field of Classification Search
 CPC .......................... G01R 33/543; G01R 33/3607; G01R 33/583; G01R 33/288; A61B 5/055
 See application file for complete search history.

(56) References Cited

U.S. PATENT DOCUMENTS

2018/0067177 A1*  3/2018  Ludwig .............. G01R 33/5608
2023/0243903 A1   8/2023  Beck et al.

FOREIGN PATENT DOCUMENTS

DE      102020208661 A1    7/2021
DE      102022200942 A1    8/2023

OTHER PUBLICATIONS

Beck, Thomas. International Standard—Publication IEC 60601-2-33 (Edition 3.2 Jun. 2015). Medical Electrical Equipment. ISBN 978-2-8322-2743-5. Mar. 22, 2022. pp. 1-548.
Beck, Thomas; International Standard—IEC 62304. Medical device software—Software life cycle processes. Edition 1.1. Jun. 2015. pp. 1-176.

(Continued)

*Primary Examiner* — G.M. A Hyder
(74) *Attorney, Agent, or Firm* — Lempia Summerfield Katz LLC

(57)         ABSTRACT

A method for generating a modified magnetic resonance sequence, a magnetic resonance device, and a computer program product are provided. In accordance with the method, an original magnetic resonance sequence is provided for the acquisition of magnetic resonance signals. The magnetic resonance sequence includes multiple gradient pulses. Further, at least one limit value is provided. At least one modification gradient pulse of the multiple gradient pulses is modified as a function of the at least one limit value, and thus, a modified magnetic resonance sequence is generated.

18 Claims, 2 Drawing Sheets

(56) References Cited

OTHER PUBLICATIONS

Heismann, Björn, Martin Ott, and David Grodzki. "Sequence-based acoustic noise reduction of clinical MRI scans." Magnetic resonance in medicine 73.3 (2015): 1104-1109.

International Standard—Publication IEC 60601-1 (Third edition—2005) I-SH 02. Medical Electrical Equipment ISBN 2-8318-8400-4. Oct. 15, 2019 pp. 1-792.

International Electrotechnical Commission—IEC CDV1 60601-2-33 ED 4.0. 2021. pp. 1-133.

* cited by examiner

1

METHOD FOR GENERATING A MODIFIED
MAGNETIC RESONANCE SEQUENCE,
MAGNETIC RESONANCE DEVICE, AND
COMPUTER PROGRAM PRODUCT

This application claims the benefit of German Patent Application No. DE 10 2022 213 010.3, filed on Dec. 2, 2022, which is hereby incorporated by reference in its entirety.

BACKGROUND

The present embodiments relate to a method for generating a modified magnetic resonance sequence, a magnetic resonance device, and a computer program product.

In medical engineering, imaging using magnetic resonance (MR) (e.g., magnetic resonance imaging (MRI)) is characterized by high soft tissue contrasts. In this case, a patient is typically positioned in an examination space of a magnetic resonance device. During a magnetic resonance scan, radio-frequency (RF) pulses are normally beamed into the patient with the help of a radio-frequency antenna unit. Further, gradient pulses are switched with the help of a gradient pulse unit. As a result of this, magnetic field gradients are generated in the examination space. Due to the generated transmission pulses, nuclear spins are excited in the patient. As a result of this, position-encoded magnetic resonance signals are triggered. The magnetic resonance signals are received by a receiving unit and are used for the reconstruction of magnetic resonance images.

For the operation of the magnetic resonance device to be safe for the patient, the RF energy absorbed by the patient (e.g., the specific absorption rate (SAR)) is not to be too high. Further, an overly strong stimulation of the patient may occur due to an overly sudden change in the magnetic field and/or strong magnetic field gradients (e.g., caused by switching of a gradient pulse).

SUMMARY AND DESCRIPTION

The scope of the present invention is defined solely by the appended claims and is not affected to any degree by the statements within this summary.

The present embodiments may obviate one or more of the drawbacks or limitations in the related art. For example, patient safety may be increased during operation of a magnetic resonance device. As another example, a magnetic resonance scan of patients, for which especially high safety-related specifications exist, may be enabled.

A computer-implemented method for generating a modified magnetic resonance sequence for operating a magnetic resonance device is provided. In this case, an original magnetic resonance sequence is provided for acquisition of magnetic resonance signals (e.g., in the form of a dataset). The original magnetic resonance sequence includes multiple gradient pulses (e.g., the magnetic resonance sequence provides multiple gradient pulses being switched by the magnetic resonance device). Further, at least one boundary condition (e.g., at least one, such as an upper and/or maximum limit value) is provided. The at least one boundary condition is provided, for example, in the form of a further dataset. At least one of the multiple gradient pulses (e.g., a "modification gradient pulse") is modified as a function of the at least one boundary condition (e.g., the at least one limit value), and thus, a modified magnetic resonance sequence is generated (e.g., in the form of a dataset).

The method may not require any changes to the hardware of currently commonplace magnetic resonance devices. Further, existing sequence implementations may continue to be used. The modified magnetic resonance sequence may be generated automatically (e.g., without intervention by an operative of the magnetic resonance device). Thanks to the selective modification of the magnetic resonance sequence unnecessarily high conservative safety measures, which may potentially reduce the performance of the magnetic resonance scan, may be prevented.

The modified magnetic resonance sequence may be provided as a dataset for the operation of the magnetic resonance device. The operation of the magnetic resonance device may include a performance of a magnetic resonance scan of a patient (e.g., an acquisition of magnetic resonance signals) based on the modified magnetic resonance sequence. Magnetic resonance signals may be acquired by the magnetic resonance device based on the modified magnetic resonance sequence. In one embodiment, during the operation of the magnetic resonance device, the at least one boundary condition (e.g., the at least one limit value) is adhered to. A magnetic resonance scan of a patient may then be performed only if in this case the at least one boundary condition (e.g., the at least one limit value) is (e.g., probably) being adhered to. As a result, the safety of the patient may be increased during the operation of the magnetic resonance sequence.

The at least one boundary condition (e.g., the at least one limit value) may describe a maximum change rate of a magnetic field to be generated by the magnetic resonance device during the performance of a magnetic resonance scan (e.g., acting in a region of the body of the patient), and/or a maximum change rate of a magnetic field gradient to be generated by the magnetic resonance device during the performance of a magnetic resonance scan (e.g., acting in the region of the body of the patient; a gradient slew rate), and/or a maximum strength of a magnetic field gradient to be generated by the magnetic resonance device during the performance of a magnetic resonance scan (e.g., acting in the region of the body of the patient).

The maximum change rate of a magnetic field to be generated, dB/dt, may, for example, be expressed in the physical unit "T/s". The maximum change rate of a magnetic field gradient to be generated, dB/ds/dt, may, for example, be expressed in the physical unit "T/m/s". The maximum strength of the magnetic field gradient to be generated, AB, may, for example, be expressed in the physical unit "T/m". The maximum magnetic field gradient may, for example, be relevant in the environment of an end (e.g., of a funnel) of a bore, in the magnetic resonance device. A magnetic field or gradient magnetic field (e.g., a time-variable magnetic field or gradient magnetic field) such as this may in each case be generated by switching one of the multiple gradient pulses. By adhering to the at least one boundary condition (e.g., the at least one limit value), an excessive stimulation in the body of the patient may, for example, be prevented.

The at least one boundary condition (e.g., the at least one limit value) may be patient-specific (e.g., the at least one boundary condition, such as the at least one limit value, is dependent on the patient to be examined). The at least one boundary condition (e.g., the at least one limit value) may be dependent on a property of the patient to be examined. For example, the at least one boundary condition (e.g., the at least one limit value) is dependent on whether an implant is arranged in the body of the patient. For example, in the case of a person with an implant, a limit value that is smaller and/or more conservative and/or more difficult to adhere to is specified than in the case of a patient without an implant. As a result, the magnetic resonance sequence may be modified patient-specifically (e.g., optimized). The method is, for example, advantageous for the MR examination of patients with conditionally MR-compatible implants (e.g., MR conditional).

The at least one modification gradient pulse may be modified such that during the performance of a magnetic resonance scan based on the modified magnetic resonance sequence, the change rate of the magnetic field to be generated and/or the change rate of the magnetic field gradient to be generated and/or the strength of the magnetic field gradient to be generated is reduced. For example, the at least one modification gradient pulse is modified such that during the performance of a magnetic resonance scan based on the modified magnetic resonance sequence, the at least one boundary condition (e.g., the at least one limit value) is adhered to.

The at least one modification gradient pulse may be modified such that the gradient moment of the modification gradient pulse remains unchanged. The gradient moment may be a temporal integral over the amplitude of the gradient pulse.

The modification of the at least one modification gradient pulse may leave unchanged an evolution of the magnetic resonance signals during the performance of a magnetic resonance scan based on the modified magnetic resonance sequence in comparison to a magnetic resonance scan based on the original magnetic resonance sequence.

The method may further include an identification of at least a first section of the magnetic resonance sequence that may be changed. The at least one first section includes the at least one modification gradient pulse and an identification of at least a second section of the magnetic resonance sequence that is to be left unchanged.

For example, a magnetic resonance sequence (e.g., the original magnetic resonance sequence and the modified magnetic resonance sequence) includes multiple sections (e.g., sequence building blocks). Such a section or sequence building block may be a logically cohesive region of the magnetic resonance sequence that includes at least one gradient pulse. Such a section may potentially still include further sequence modules, such as, for example, an excitation module (e.g., an RF pulse for the excitation of magnetic resonance signals) and/or a readout module (e.g., for reading out magnetic resonance signals).

Sections to be left unchanged may be sections in which a modification of a gradient pulse contained therein would result in a change in the magnetic resonance signals, were a magnetic resonance scan to be performed in accordance with the changed magnetic resonance sequence.

The at least one second section may include at least one time period, in which it is provided for at least one radio-frequency pulse to be transmitted and/or at least one magnetic resonance signal to be received and/or at least one flow compensation gradient pulse to be switched and/or at least one diffusion gradient pulse to be switched. In such time periods, no change may be made in the gradient pulse, in order not to influence the evolution of the signal.

The modification of the at least one modification gradient pulse may include a, for example, temporal smoothing and/or a, for example, temporal stretching of the at least one modification gradient pulse. For example, the gradient pulse in question is extended.

For example, a time period in the magnetic resonance sequence is identified in which little or no gradient activity (e.g., gradient amplitude) is specified; in this time period, the gradient activity (e.g., gradient amplitude) is increased, and simultaneously, in another time period with originally high gradient activity, the gradient activity (e.g., gradient amplitude) is reduced. For example, the shape of the gradient pulse is leveled off. For example, sudden changes in amplitude in the profile of the gradient pulse are prevented. The change rate (e.g., the rate of increase and/or the rate of decrease) of the gradient pulse or of the associated magnetic field may be reduced.

The method may further include a performance of a magnetic resonance scan based on the modified magnetic resonance sequence, and monitoring (e.g., in real time) during the performance of the magnetic resonance scan based on the modified magnetic resonance sequence, whether the at least one boundary condition (e.g., the at least one limit value) is being adhered to. Monitoring in real time may be continuous monitoring in which a monitoring result is available immediately after a processing time required therefor (e.g., as a function of a computing power expended therefor).

The magnetic resonance sequence may be modified during the performance of the magnetic resonance sequence (e.g., at the runtime thereof). If, due to the monitoring, it transpires that the at least one boundary condition (e.g., the at least one limit value) is (probably) not being adhered to, the modification of the at least one modification gradient pulse may take place. This form of embodiment may, for example, have the advantage that the magnetic resonance sequence need not be present in full at the time of the commencement of the magnetic resonance scan. One possible application that may profit therefrom is, for example, interventions in which the surgeon would like to change the protocol parameters in order optimally to navigate an intervention needle during the performance of a biopsy.

The modification of the at least one modification gradient pulse may take place in a trustworthy component of the magnetic resonance device.

An encapsulated implementation of the gradient manipulation in a trustworthy component may enable an implementation in higher software safety classes in comparison to the implementation of the magnetic resonance sequence. For example, the magnetic resonance sequence and scan activation software may continue to be implemented in Software Class B (e.g., in accordance with IEC 62304), whereas in contrast, the implementation of the gradient manipulation takes place as Software Class C.

The trustworthy component (TC) may be configured to be arranged in a control path (C path) (e.g., a safety-related function) of a magnetic resonance device, so that when the TC is arranged in the control path, control information processed in the control path (e.g., for controlling a gradient pulse unit of the magnetic resonance device) in a section of the control path following (e.g., immediately after) the at least one TC has at least one predetermined (e.g., guaranteed) property. The safety-related function may, for example, include control of a gradient pulse unit of the magnetic resonance device. This following section of the control path may, for example, include a gradient pulse unit of the magnetic resonance device that is suitable for generating gradient pulses.

For example, the at least one TC is configured so that when the TC is arranged in the control path, the control information processed in the control path, and, for example, output by the TC, is arranged at a location at which the at least one TC is arranged in the control path that has at least one predetermined property. The predetermined property may provide that during the performance of a magnetic resonance scan based on the modified magnetic resonance sequence, the at least one boundary condition (e.g., the at least one limit value) is adhered to.

The at least one TC may have a signal input, with which the control information (e.g., coming from a further component of the control path) may be received. The at least one TC may have a signal output, with which the control information may be output to a further component of the control path. Adherence to at least one property of the control information processed in the control path may be guaranteed at the signal output of the TC.

The TC may forward the control information to the signal output of the TC, after successfully checking a signal input of the TC; should the check not be successful, an appropriate measure is taken. Depending on the task of the TC, this measure may, for example, be the cancellation of the execution of the control information or a modification of the control information.

If, for example, this check establishes that the at least one boundary condition (e.g., the at least one limit value) is not being adhered to, the appropriate measure may include modifying the at least one modification gradient pulse as a function of the at least one boundary condition (e.g., the at least one limit value). For example, the measure may include not performing a magnetic resonance scan, as long as no modification of the magnetic resonance sequence is possible that results in adherence to the at least one boundary condition (e.g., of the at least one limit value).

The cancellation of the performance of the control information may, for example, take place using a "hard cancellation" that may, for example, include interrupting the flow of control information and/or outputting an error message to an operative of the magnetic resonance device.

A possible modification of the control information may, for example, include a transfer (e.g., preceding transfer) of the control information to modified control information that satisfies the required properties. This modified control information may in the context of IEC 60601-2-33, for example, satisfy the properties of a safe status. As long as a modification of the control information permits a continuation of the scan, the cancellation of the scan may be prevented.

With the help of the control information and/or a stream of control information, a control command may be executed and/or a control task is performed. The at least one TC may be a component as part of a processing chain of the control information (e.g., of a stream of control information). The at least one predetermined property may be a quantifiable and/or safety-related property. The TC may check that in accordance with the control information the at least one boundary condition (e.g., the at least one limit value) is being adhered to (e.g., the at least one predetermined property may relate to the adherence to such specified boundary conditions, such as limit values). The at least one predetermined property may, for example, relate to a limit of an activity of the magnetic resonance device, such as, for example, a limit of a gradient activity (e.g., for adherence to stimulation thresholds for the patient's heart and/or peripheral nervous system (PNS)).

In one embodiment, this relates to an activity that is likely to cause damage to persons (e.g., to the patient being examined by the magnetic resonance examination) and/or damage to equipment (e.g., to the magnetic resonance device).

For example, the TC is configured so that when the TC is arranged in the control path, the control path is at least in part not necessarily trustworthy or need not be trustworthy. The not necessarily trustworthy section of the control path is referred to below for short as the "non-trustworthy section." The TC may be understood as a barrier that divides the control path into a trustworthy section and a non-trustworthy section. The non-trustworthy section of the control path may be characterized in that the non-trustworthy section is subject to fewer demands for the development and/or operation of the safety-related function. In the case of a non-trustworthy section, it is not necessary to guarantee a correct calculation of control information within this section of the control path.

The control path may have a processing chain of the control information and/or a stream of control information for the control of a safety-related function of the control path. This function may, for example, be a control task for the performance of a magnetic resonance sequence. For example, the control path is the carrier of a stream of control information. With the help of the control information and/or the stream of control information, a safety-related function may be controlled. The control information and/or the stream of control information, for example, describes at least one part of a magnetic resonance sequence (e.g., the provided original magnetic resonance sequence). The control information and/or the stream of control information may, for example, be initiated by a command source unit in the control path (e.g., a system control unit of the magnetic resonance device). The command source unit may, for example, be a first and/or initial element of a processing chain of the control information in the control path. The original magnetic resonance sequence may, for example, be assigned by a command source unit.

The control path may, for example, include elements that contribute to a controlled operation of the safety-related function of the magnetic resonance device. For example, the control path implements an execution of the safety-related function. For example, the control path implements a correct execution of functions in which there is a safety-related element. This provides, for example, that an erroneous execution of such a function may entail damage to patient and/or equipment.

Any protect paths (P paths) of the magnetic resonance device may be differentiated from the control path. These may, for example, include elements that contribute to monitoring of the (e.g., safety-related) function of the control path. For example, protect paths may include sensors and/or detectors for the capture of a safety-related parameter.

Further, a magnetic resonance device that is configured to execute an above-described method is provided. The magnetic resonance device may, for example, have a system control unit for the provision and/or receipt of an original magnetic resonance sequence for the acquisition of magnetic resonance signals and for the provision and/or receipt of at least one boundary condition (e.g., a limit value). Further, the system control unit may be configured to generate a modified magnetic resonance sequence by modification of at least one modification gradient pulse from the multiple gradient pulses as a function of the at least one boundary condition (e.g., the at least one limit value). The system control unit may, for example, have a computing unit including, for example, one or more processors, and/or a memory unit including, for example, one or more memory modules. The advantages of the magnetic resonance device substantially correspond to the advantages of the computer-implemented method for generating a modified magnetic resonance sequence for operating a magnetic resonance device, which have been explained above in detail.

Further, a computer program product that includes a program and may be loaded directly into a memory of a programmable system control unit of a magnetic resonance device and has program means (e.g., libraries and auxiliary functions) is provided in order to execute a method for generating a modified magnetic resonance sequence for operating a magnetic resonance device if the computer program product is executed in the system control unit of the magnetic resonance device. The computer program product may in this case include software with a source code that still has to be compiled and linked, or only has to be interpreted, or an executable software code that, for execution, only has to be loaded into the system control unit.

Thanks to the computer program product, the method may be executed quickly, identically repeatably, and robustly. The computer program product may be configured so that, using the system control unit, the computer program product may execute the method acts. The system control unit in this case in each case has the prerequisites, such as, for example, a corresponding main memory, a corresponding graphics card, or a corresponding logic unit, so that the respective method steps may be executed efficiently.

The computer program product is, for example, stored on a computer-readable medium or on a network or server, from where the computer program product may be loaded into the processor of a local system control unit that is directly connected to the magnetic resonance device or may be configured as part of the magnetic resonance device. Further, control information of the computer program product may be stored on an electronically readable data storage medium (e.g., a non-transitory computer-readable storage medium). The control information of the electronically readable data storage medium may be configured such that when the data storage medium is used in a system control unit of a magnetic resonance device the control information performs a method.

Examples of electronically readable data storage media are a DVD, a magnetic tape, or a USB stick, on which electronically readable control information (e.g., software) is stored. If this control information is read from the data storage medium and is stored in a system control unit of the magnetic resonance device, all forms of embodiment of the above-described methods may be performed.

Further advantages, features, and details of the invention emerge from the embodiments described below and based on the drawings. Parts corresponding to one another are provided with the same reference characters in all the figures.

DETAILED DESCRIPTION

Figure 1:
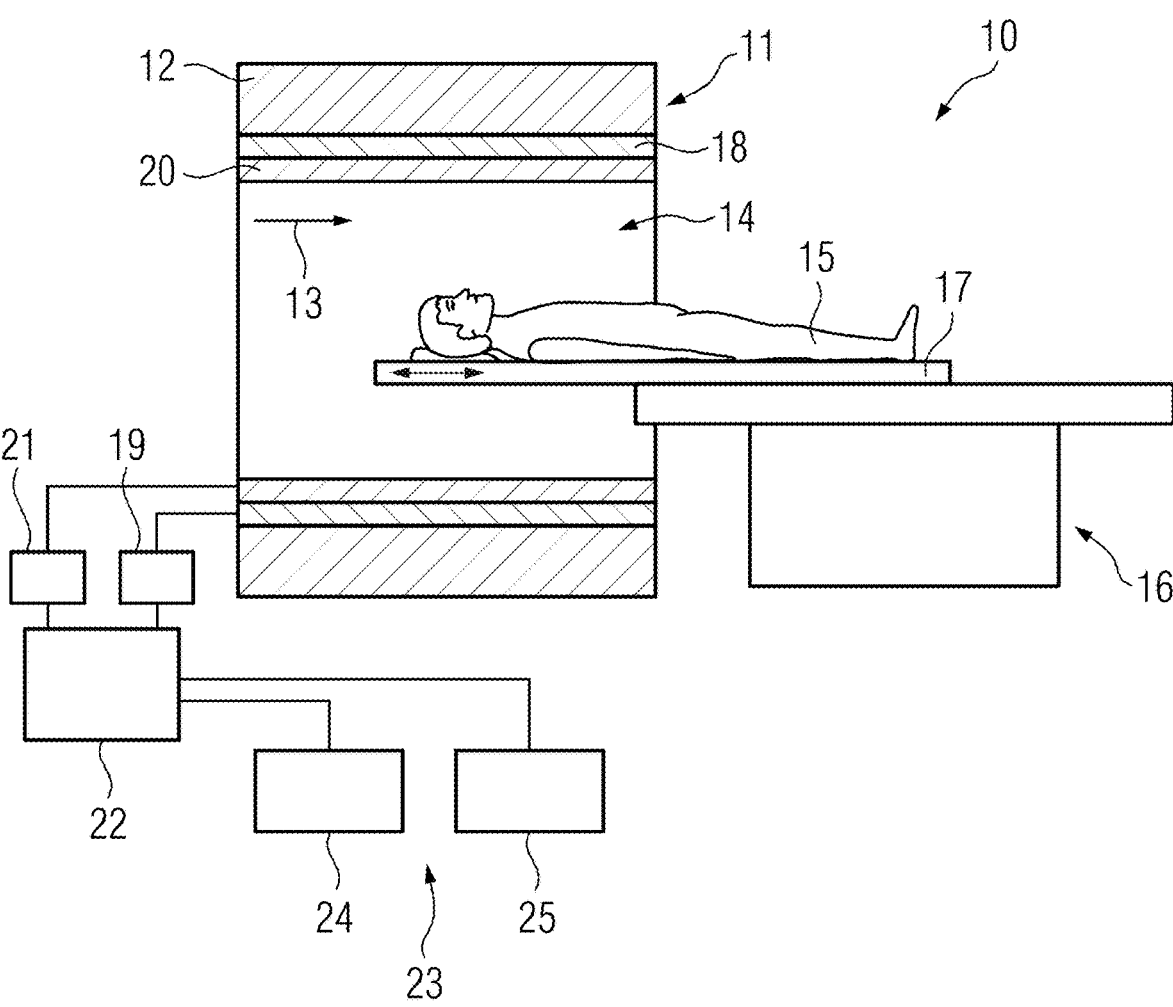
FIG. 1 shows a magnetic resonance device in a schematic representation.

FIG. 1 schematically represents a magnetic resonance device 10. The magnetic resonance device 10 includes a magnet unit 11 that has a main magnet 12 for generation of a strong and, for example, temporally constant main magnetic field 13. Further, the magnetic resonance device 10 includes a patient receiving area 14 for receipt of a patient 15. The patient receiving area 14 in the present embodiment is configured to be cylindrical and is surrounded cylindrically in a peripheral direction by the magnet unit 11. However, in principle, a design of the patient receiving area 14 deviating from this may be provided. The patient 15 may be pushed into the patient receiving area 14 by a patient positioning device 16 of the magnetic resonance device 10. For this purpose, the patient positioning device 16 has a patient table 17 that is movably configured inside the patient receiving area 14.

The magnet unit 11 further has a gradient pulse unit 18 for generation of gradient pulses. In accordance with the gradient pulses, magnetic field gradients or gradient fields that are used for position encoding during imaging are generated. The gradient pulse unit 18 may, for example, include three gradient coils, each of which may generate a magnetic field gradient in another spatial direction (e.g., an x-gradient coil for the x-direction, a y-gradient coil for the y-direction, and a z-gradient coil for the z-direction). The gradient pulse unit 18 is controlled by a gradient coil unit 19 of the magnetic resonance device 10.

The magnet unit 11 further includes a radio-frequency antenna unit 20 that, in the present embodiment, is configured as a body coil permanently integrated into the magnetic resonance device 10. The radio-frequency antenna unit 20 is controlled by a radio-frequency antenna control unit 21 of the magnetic resonance device 10 and beams radio-frequency magnetic resonance sequences into an examination space that is substantially formed by a patient receiving area 14 of the magnetic resonance device 10. This causes an excitation of atomic nuclei to occur in the main magnetic field 13 generated by the main magnet 12. Due to relaxation of the excited atomic nuclei, magnetic resonance signals are generated. The radio-frequency antenna unit 20 is configured to receive the magnetic resonance signals.

The magnetic resonance device 10 has a system control unit 22 for control of the main magnet 12, the gradient coil unit 19, and the radio-frequency antenna control unit 21. The system control unit 22 controls the magnetic resonance device 10 centrally, such as, for example, the performance of a predetermined magnetic resonance sequence. Further, the system control unit 22 includes an evaluation unit, not shown in greater detail, for evaluation of the magnetic resonance signals captured during the magnetic resonance examination. Further, the magnetic resonance device 10 includes a user interface 23 that is connected to the system control unit 22. Control information, such as imaging parameters, for example, as well as reconstructed magnetic resonance images, may be displayed on a display unit 24 (e.g., on at least one monitor) of the user interface 23 for a medical operative. Further, the user interface 23 has an input unit 25, using which information and/or parameters may be input by the medical operative during a scan procedure.

Figure 2:
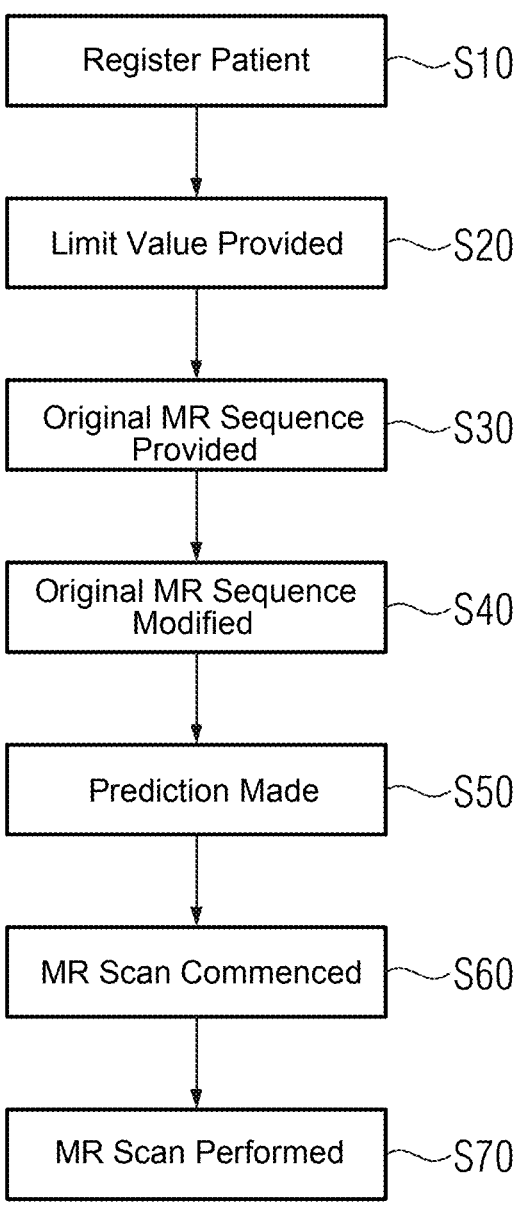
FIG. 2 shows a method for the operation of the magnetic resonance device.

FIG. 2 shows a method for the operation of the magnetic resonance device (e.g., for the generation of a modified magnetic resonance sequence).

For example, a method is provided for limiting a maximum change in the gradient field. This method may be embedded in a work sequence for the examination of a patient 15 who has an implant. The sequence shown in FIG. 2 is greatly simplified; a plurality of scans may also be performed, and acts may also be performed multiple times or just in part and also in another order.

In S10, a patient is registered. For example, in this case, the mass of the patient and other properties of the patient relevant to the subsequent scan are captured. This, for example, includes the property of whether or not the patient has an implant. For example, in the course of patient registration, an operative of the magnetic resonance device 10 activates a dedicated operating mode for the operation of the magnetic resonance device 10 (e.g., an implant mode). The magnetic resonance device 10 may be selectively and/or dedicatedly put into a status such that the above-described method is to be applied, and the limit values to be monitored have been input by the operative.

For example, account may be taken here of what type of implant the patient has. As a function of the type of implant, it is, for example, possible to establish which requirements (e.g., limitations and/or limit values to be adhered to) are to be taken into account in the subsequent magnetic resonance scan. These limitations may, for example, be specified in an implant pass associated with the implant.

In S20, at least one limit value is provided. If mention is made in the rest of the description of "limit value," this may also be transposed in general to "boundary condition." This may, for example, be derived from the information captured during the patient registration. Alternatively, the at least one limit value may already be captured in S10 during the patient registration. For example, the at least one limit value may be input by the input unit 25 of the user interface 23. The at least one limit value may also, for example, include limit values relating to RF pulses, in addition to limit values relating to gradient pulses. The at least one limit value provided may, for example, be more conservative than a possible limitation specified in an implant pass.

In S30, an original magnetic resonance sequence for the acquisition of magnetic resonance signals is provided, which includes multiple gradient pulses. To this end, a scan protocol may be selected and/or adjusted, for example, with the help of the input unit 25 of the user interface 23. Besides the multiple gradient pulses, the original magnetic resonance sequence may include further sequence modules.

In S40, the original magnetic resonance sequence is modified, and thus, a modified magnetic resonance sequence is generated. In this case, at least one gradient pulse, referred to as a "modification gradient pulse" below, is modified as a function of the at least one limit value by the multiple gradient pulses of the original magnetic resonance sequence.

In this case, for example, the temporal description of the original magnetic resonance sequence is split into sections, there being two types of sections.

The first type of temporal sections includes time periods that may be modified, since in these time periods, for example, only the integral of the gradient pulse (e.g., the gradient moment) is relevant to imaging. In these sections, a modification may, therefore, be made for adherence to the specified limit values (e.g., implant limit values) with respect to the gradient field. For this, a gradient profile is selected that is advantageous with respect to the specified limit value. This may be the case for a performance of the gradient coil that has been smoothed and temporally stretched as much as possible.

The second type of temporal sections includes time periods in which RF pulses are emitted or generated magnetic resonance signals are received and/or read out. Also falling in this category are temporal sections that are used for flow compensation. No change in the gradient pulse is to be made in these time periods in order not to influence the signal evolution. In S40, therefore, at least one second section of the magnetic resonance sequence that is to be left unchanged is identified.

The adjustment of the magnetic resonance scan in S40 may take place in a trustworthy component. As a result, it may be possible to perform the modification of the magnetic resonance scan and thus to mitigate the underlying risk from difficulty level 3 in the requisite software class Con stand-alone hardware.

After the, for example, automatic modification of the magnetic resonance sequence in S40, a prediction in S50 as to whether the required at least one limit value of the gradient field may probably be adhered to may be made. This act is advantageous because potentially overshoots of limit values are situated in time sections that cannot be changed, so that by adjusting the magnetic resonance scan in S40, it is also not possible to achieve any conformity with the limit value provided in S20. So long as this check is successful, the pulse sequence may be transferred to the scan system for performance, and the magnetic resonance scan in S60 may be commenced.

The prediction as to whether the at least one limit value is being adhered to may be performed by a different software component from the component for control of the magnetic resonance sequence itself (e.g., for adjustment of the magnetic resonance sequence in S40). The adjustment of the magnetic resonance sequence in S40 may hence take place with significantly fewer safety requirements (e.g., with respect to safety classification of the software) than the prediction as to whether the at least one limit value is being adhered to. Hence, both these functionalities may be separated and/or segregated from one another. As a result, it may be possible to prevent possible increased requirements of the safety-critical check being transferred to the remaining software.

During a performance of the magnetic resonance scan in S70, further monitoring of the at least one limit value may take place in real time in order to provide that the at least one limit value is not exceeded using a second, independent monitoring mechanism. This monitoring may, for example, include monitoring of electrical currents flowing through the gradient coils of the gradient pulse unit 18.

An adjustment of the magnetic resonance sequence in S70 is advantageous because magnetic resonance scanning at the time of the commencement of the scan in S60 need not be present in full. Thus, for example, there are magnetic resonance sequences that are modified at runtime in order to adjust sequence parameters such as echo times or similar. One application of this, for example, is interventions in which the surgeon would like to change the sequence parameters in order optimally to navigate an intervention needle during the performance of a biopsy.

The methods described in detail above and the magnetic resonance device relate solely to embodiments that may be modified by the person skilled in the art in a variety of ways, without departing from the scope of the invention. Further, the use of the indefinite article "a" or "an" does not rule out that the features in question may also be present multiple times. Likewise, the term "unit" does not rule out that the components in question consist of multiple interacting sub-components that, if appropriate, may also be distributed spatially.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A computer-implemented method for generating a modified magnetic resonance sequence for operating a magnetic resonance device, the computer-implemented method comprising:

providing an original magnetic resonance sequence for acquisition of magnetic resonance signals, wherein the original magnetic resonance sequence comprises multiple gradient pulses;

providing at least one boundary condition; and generating the modified magnetic resonance sequence, the generating of the modified magnetic resonance sequence comprising modifying at least one modification gradient pulse from the multiple gradient pulses as a function of the at least one boundary condition, wherein the modification of the at least one modification gradient pulse leaves unchanged an evolution of the magnetic resonance signals during performance of a magnetic resonance scan based on the modified magnetic resonance sequence compared to a magnetic resonance scan based on the original magnetic resonance sequence.

2. The computer-implemented method of claim 1, wherein providing the at least one boundary condition comprises providing a limit value.

3. The computer-implemented method of claim 1, wherein the at least one boundary condition describes a maximum change rate of a magnetic field to be generated, a maximum change rate of a magnetic field gradient to be generated, a maximum strength of a magnetic field gradient to be generated, or any combination thereof.

4. The computer-implemented method of claim 1, wherein the at least one boundary condition is dependent on a patient to be examined.

5. The computer-implemented method of claim 4, wherein the at least one boundary condition is dependent on an implant arranged in a body of the patient.

6. The computer-implemented method of claim 1, wherein the at least one modification gradient pulse is modified such that during performance of a magnetic resonance scan based on the modified magnetic resonance sequence, a temporal change rate of a magnetic field is reduced.

7. The computer-implemented method of claim 1, wherein the at least one modification gradient pulse is modified such that during performance of a magnetic resonance scan based on the modified magnetic resonance sequence, the at least one boundary condition is adhered to.

8. The computer-implemented method of claim 1, further comprising:

identifying at least one first section of the magnetic resonance sequence that is changeable, wherein the at least one first section comprises the at least one modification gradient pulse; and identifying at least one second section of the magnetic resonance sequence that is to be left unchanged.

9. The computer-implemented method of claim 8, wherein the at least one second section comprises at least one time period in which it is provided for at least one radio-frequency pulse to be transmitted, at least one magnetic resonance signal to be received, at least one flow compensation gradient pulse to be switched, at least one diffusion gradient pulse to be switched, or any combination thereof.

10. The computer-implemented method of claim 1, wherein modifying the at least one modification gradient pulse comprises a smoothing, stretching, or smoothing and stretching of the at least one modification gradient pulse.

11. The computer-implemented method of claim 1, further comprising:

performing a magnetic resonance scan based on the modified magnetic resonance sequence; and monitoring during the performing of the magnetic resonance scan based on the modified magnetic resonance sequence as to whether the at least one boundary condition is being adhered to.

12. The computer-implemented method of claim 1, wherein the modifying of the at least one modification gradient pulse takes place in a component of the magnetic resonance device that is configured to be arranged in a control path of the magnetic resonance device.

13. A magnetic resonance device configured to generate a modified magnetic resonance sequence for operating a magnetic resonance device, the magnetic resonance device being configured to generate the modified magnetic resonance sequence comprising the magnetic resonance device being configured to:

provide an original magnetic resonance sequence for acquisition of magnetic resonance signals, wherein the original magnetic resonance sequence comprises multiple gradient pulses;

provide at least one boundary condition; and generate the modified magnetic resonance sequence, the generation of the modified magnetic resonance sequence comprising modification of at least one modification gradient pulse from the multiple gradient pulses as a function of the at least one boundary condition, wherein the modification of the at least one modification gradient pulse leaves unchanged an evolution of the magnetic resonance signals during performance of a magnetic resonance scan based on the modified magnetic resonance sequence compared to a magnetic resonance scan based on the original magnetic resonance sequence.

14. In a non-transitory computer-readable storage medium that stores instructions executable by one or more processors to generate a modified magnetic resonance sequence for operating a magnetic resonance device, the instructions comprising:

providing an original magnetic resonance sequence for acquisition of magnetic resonance signals, wherein the original magnetic resonance sequence comprises multiple gradient pulses;

providing at least one boundary condition; and generating the modified magnetic resonance sequence, the generating of the modified magnetic resonance sequence comprising modifying at least one modification gradient pulse from the multiple gradient pulses as a function of the at least one boundary condition, wherein the modification of the at least one modification gradient pulse leaves unchanged an evolution of the magnetic resonance signals during performance of a magnetic resonance scan based on the modified magnetic resonance sequence compared to a magnetic resonance scan based on the original magnetic resonance sequence.

15. The non-transitory computer-readable storage medium of claim 14, wherein providing the at least one boundary condition comprises providing a limit value.

16. The non-transitory computer-readable storage medium of claim 14, wherein the at least one boundary condition describes a maximum change rate of a magnetic field to be generated, a maximum change rate of a magnetic field gradient to be generated, a maximum strength of a magnetic field gradient to be generated, or any combination thereof.

17. The non-transitory computer-readable storage medium of claim 14, wherein the at least one boundary condition is dependent on a patient to be examined.

18. The non-transitory computer-readable storage medium of claim 14, wherein the at least one modification gradient pulse is modified such that during performance of a magnetic resonance scan based on the modified magnetic resonance sequence, a temporal change rate of a magnetic field is reduced.

* * * * *